US012491294B2

(12) United States Patent
Marra et al.

(10) Patent No.: US 12,491,294 B2
(45) Date of Patent: Dec. 9, 2025

(54) PERITONEAL DIAYLSIS SYSTEM AND CASSETTES THEREFOR

(71) Applicant: Bellco S.R.L., Mirandola (IT)

(72) Inventors: Antonio Giuseppe Marra, Bologna (IT); Salvatore Orlandini, Fontanafredda (IT); Guilherme Pagatini, Mirandola (IT); Alberto Petrucci, L'Aquila (IT); Mariachiara Ricci, Rome (IT); Arianna Roma, Mirandola (IT); Andrea Veratti, Modena (IT)

(73) Assignee: Bellco S.R.L., Mirandola (IT)

( * ) Notice: Subject to any disclaimer, the term of this patent is extended or adjusted under 35 U.S.C. 154(b) by 861 days.

(21) Appl. No.: 17/505,336

(22) Filed: Oct. 19, 2021

(65) Prior Publication Data

US 2022/0126006 A1 Apr. 28, 2022

(30) Foreign Application Priority Data

Oct. 28, 2020 (EP) .................................... 20204331

(51) Int. Cl.
*A61M 1/14* (2006.01)
*A61M 1/16* (2006.01)
(Continued)

(52) U.S. Cl.
CPC .............. *A61M 1/159* (2022.05); *A61M 1/15* (2022.05); *A61M 1/155* (2022.05); *A61M 1/156* (2022.05);
(Continued)

(58) Field of Classification Search
CPC .......... A61M 1/14; A61M 1/15; A61M 1/153; A61M 1/154; A61M 1/155; A61M 1/156; A61M 1/1561; A61M 1/1565; A61M 1/1566; A61M 1/159; A61M 1/1654; A61M 1/1656; A61M 1/1666; A61M 1/28; A61M 1/282; A61M 1/287; A61M 1/288; A61M 2039/0027; A61M 2205/12;
(Continued)

(56) References Cited

U.S. PATENT DOCUMENTS

| | | | | |
|---|---|---|---|---|
| 7,935,074 | B2 * | 5/2011 | Plahey | A61M 1/28 604/29 |
| 2017/0319768 | A1 * | 11/2017 | Szpara | A61M 1/1605 |
| 2019/0262522 | A1 * | 8/2019 | Wyeth | A61M 1/1696 |

FOREIGN PATENT DOCUMENTS

| | | | | |
|---|---|---|---|---|
| WO | WO-0057935 | A1 * | 10/2000 | A61L 2/0023 |

* cited by examiner

*Primary Examiner* — Shefali D Patel

(57) ABSTRACT

A peritoneal dialysis system includes a preparator and a cycler. The system delivers purified water into one or more containers with different powders to create a concentrate and then moves the concentrate to a mixing bag to create a peritoneal dialysis fluid (PDF). The cycler then delivers the PDF to a patient and removes waste fluid via a drain outlet. A volumetric approach controls hydraulic fluid paths that introduce the purified water to the powders to create the concentrate, provide mixing of the concentrate to form the PDF and deliver the PDF to the patient. Different configurations of hydraulic flow/pressure generators are provided in the fluid paths to provide optimization of flow of the purified water through the system to create correct concentrates from the powders and subsequent peritoneal dialysis fluid for cycling, for example being provided in a disposable cassette.

17 Claims, 13 Drawing Sheets

(51) Int. Cl.
*A61M 1/28* (2006.01)
*A61M 5/14* (2006.01)

(52) U.S. Cl.
CPC ........ *A61M 1/1565* (2022.05); *A61M 1/1566* (2022.05); *A61M 1/1656* (2013.01); *A61M 1/28* (2013.01); *A61M 1/282* (2014.02); *A61M 1/287* (2013.01); *A61M 5/1409* (2013.01); *A61M 1/153* (2022.05); *A61M 1/154* (2022.05); *A61M 1/1561* (2022.05); *A61M 1/288* (2014.02); *A61M 2205/12* (2013.01)

(58) Field of Classification Search
CPC ...... A61M 2205/127; A61M 2205/128; A61M 2205/36; A61M 2210/1017
See application file for complete search history.

PERITONEAL DIAYLSIS SYSTEM AND CASSETTES THEREFOR

This application claims priority from European Patent Application No. 20204331.1, filed Oct. 28, 2020, and entitled, "PERITONEAL DIALYSIS SYSTEM AND CASSETTES THEREFOR," the entire content of which is incorporated herein by reference.

FIELD

The present invention relates to a peritoneal dialysis system and to cassettes for providing fluid connections and paths within such a dialysis system.

BACKGROUND

One type of dialysis for the treatment of kidney failure is peritoneal dialysis (PD) which uses the lining of a patient's abdomen, the peritoneum, to filter blood while its remains inside the body. Peritoneal Dialysis is an effective way to treat patients with End Stage Renal Disease and acute patients with renal failure. The patient is provided with a catheter that includes a transfer set for selective connection to a dialysis solution or a drain bag. A dialysis solution ('dialysate' or 'peritoneal dialysis fluid') comprising water with other electrolytes is warmed to body temperature and then introduced into the peritoneal cavity of the patient via the catheter. The solution remains here for a period of time required to clean the blood of waste products, toxins and excess fluid and these are then removed from the body to leave the right amounts of electrolytes and nutrients in the blood. The machine or 'cycler' may repeat the exchange process a number of times (cycles), as required for a particular patient.

Conventionally dialysate consists of purified water, glucose and electrolytes, with the concentration of electrolytes resembling that which occurs naturally in the blood. It is prepared according to an individual patient's needs to help regulate their electrolyte and acid-base balance and remove metabolic waste products. The dialysate components are normally shipped in the form of concentrates, with basic and acidic concentrates being prepared separately. The basic concentrate is usually supplied as a dry concentrate consisting of pure sodium bicarbonate which is made up into a saturated solution and the acidic concentrate is usually provided as a liquid concentrate. If it is provided as a dry concentrate, the entire concentrate must be dissolved before being diluted to form the dialysate. This requires a large volume of liquid and multiple components for providing the peritoneal dialysis fluid, increasing the time required for production of the fluid. Concentrate may also be wasted during the production of the correct peritoneal dialysis fluid and difficulties may be encountered in providing the correct concentration of electrolytes in the fluid for a particular patient. Thus, while it is preferable to provide the concentrates in dry form to reduce their volume for shipping and storage purposes, providing the correct dialysate for a particular patient on a continuous basis can prove problematic. As a result, multiple bags of PDF are normally provided pre-prepared for dialysis. The high weights of peritoneal dialysis fluid (PDF) bags reduces the appeal of this procedure, as does the number, volume and weight of supplies required for each daily treatment (up to 15-18 Liters every day).

It is an object of the present invention to provide an improved peritoneal dialysis system that aims to overcome or at least alleviate the above-mentioned drawbacks.

SUMMARY

A first aspect of the present invention provides a peritoneal dialysis system comprising a peritoneal dialysis preparator and cycler, the preparator comprising a purified water source fluidly connectable to a plurality of containers each containing one or more solutes for dissolution of the solutes to form peritoneal dialysis fluid for delivery to the cycler for delivery to and drainage from a patient, wherein a hydraulic flow generator is provided in at least one of the fluid paths between the water source and the containers and the containers and the cycler.

In a preferred embodiment, each container is fluidly connectable to a chamber for receiving a solution of the solutes for preparation of a peritoneal dialysis fluid, chamber being fluidly connectable to the cycler. At least one hydraulic flow generator may be provided in a fluid path between the containers and the chamber and/or the chamber and the cycler.

Preferably, the system according to the invention is provided with an arrangement of hydraulic flow or pressure generators, such as flexible pumps, throughout the fluid paths to provide optimized dissolution of the solutes, optimized mixing of the solution and/or cycling of the peritoneal dialysis fluid thus formed. It is preferable for at least one of the hydraulic flow generators to be a variable flow generator. The different configurations of hydraulic flow/pressure generators are provided in the fluid paths to provide optimization of the flow of water through the fluid system to create the correct powder concentrates and subsequent peritoneal dialysis fluid for cycling.

At least one hydraulic flow generator is preferably provided in the cycler fluid path for controlled movement of the prepared peritoneal dialysis fluid. Preferably, a hydraulic flow generator is also provided in a fluid path between the water source and the solute containers and/or the PDF chamber.

It is preferable for the at least one hydraulic flow generator in the cycler fluid path and/or between the solute container and chamber to be one that provides a high accuracy stroke to enable the required proportioning of the solution. Preferably, the flow measurement accuracy is >2% or 8-12 ml. Preferably, the hydraulic flow generator in the fluid path between the water source and the solute containers is one that provides a high flow rate to ensure complete reconstitution of the solute. Preferably, operative flow range is 50 ml/min to 400 ml/min.

Optionally, each solute container may have a hydraulic flow generator in its fluid path with the water source. In one embodiment, three solute containers are provided that are each fluidly connectable to the purified water source, with each fluid path having a hydraulic flow generator. This allows a peritoneal dialysis fluid to be generated without a mixing chamber prior to delivery to a patient.

Any suitable hydraulic flow generator may be provided, such as an actuator operable on the fluid line. A pump, such as a hydraulic piston pump or a peristaltic pump may form the hydraulic flow generator. The hydraulic flow generators may be provided within tubing extending between the component parts of the system but more preferably are included in a cassette operable within the dialysis system. A cassette may be provided in the preparator part of the system and/or the cycler part of the system. More preferably, a cassette is provided for at least the cycler part of the system.

Preferably, the cassette has appropriate inlet and outlet connections, fluid paths between the inlet and outlet connections, at least one flow generator and a plurality of valves provided in the fluid paths.

To this end, a second aspect of the present invention provides a cassette comprising at least one connector to a peritoneal dialysis fluid source, at least one connector to a patient line and at least one connector to a drainage line, said cassette having fluid paths between the connectors and including a hydraulic flow generator in at least one fluid path.

Preferably, the cassette according to the second aspect of the invention is for receipt in a cycler of the system according to the first aspect of the present invention. More preferably, the cassette has multiple connectors to each solute container, optionally a PDF bag connector, a patient line connector and a drain connector. Preferably, the cassette is provided with a single flow generator and a plurality of valves, the valves being provided in different fluid paths.

Alternatively or additionally, a cassette may be provided with a purified water source inlet for connection to a purified water source, at least one solute inlet for fluidly connecting a container of solute to a fluid path between the water source inlet and the at least one solute inlet, and an outlet for connection to a fluid path for flow of a solution formed to a peritoneal dialysis fluid chamber, the cassette having at least one hydraulic flow generator in at least one fluid path.

Preferably, at least one hydraulic flow generator is included in the fluid path between the solute inlet and the outlet to the peritoneal dialysis fluid chamber. Preferably, at least one hydraulic flow generator is provided in the fluid path of the water source inlet.

A hydraulic flow generator may also be provided in the fluid path to each solute container. Preferably, the cassette includes three solute inlets for connection to three separate solute containers or compartments of a container. Preferably, each fluid path from each solute inlet is provided with a hydraulic flow generator.

The hydraulic generator may a high accuracy or high flow rate generator depending upon its positioning in the fluid circuit. Preferably, the least one hydraulic flow generator provided in the fluid path of the water source inlet is a high flow rate generator. Preferably, the least one hydraulic flow generator provided in the fluid path of the peritoneal dialysis chamber is a high accuracy flow generator.

The cassette may be provided with other components that are conventional in the art and therefore will not be discussed here in any detail. Such components include, inter alia, a casing surrounding the fluid paths, pump regions, for example, being formed by chambers open to one side that are covered by a flexible plastic film and valve regions that may block the fluid paths. The cassette may also be provided with a heating region, such as heating elements provided in a part of the cassette that surrounds a fluid path. Sensors may also be provided within the cassette to monitor fluid flow and properties, such as temperature.

It is to be appreciated that the inlets and outlets of the cassette may be connected to other fluid paths by hose elements.

The at least one container is preferably a bag that contains one or more solutes, preferably in a concentrated form and provided in separate compartments. These concentrated solutes may for example be in the form of powder, pellets, super concentrated liquid and/or gel.

The bag preferably includes a nozzle attachment to aid mixing of the solute with the purified water.

The bag described herein may further comprise one more additional openings. The additional openings may be any shape or size. Preferably the openings in the bag are configured to allow attachment to piping or tubing, or additional nozzles. Said openings may enable solutes to be added and/or enable the solution to be removed from the bag. Additional openings may be at any position in the bag.

The invention described herein may further comprise a water purification unit configured to be fluidly connectable to the purified water source. The water purification unit may purify water taken from any source, such as mains water from a domestic tap or faucet.

DETAILED DESCRIPTION

Definitions

Figure 1:
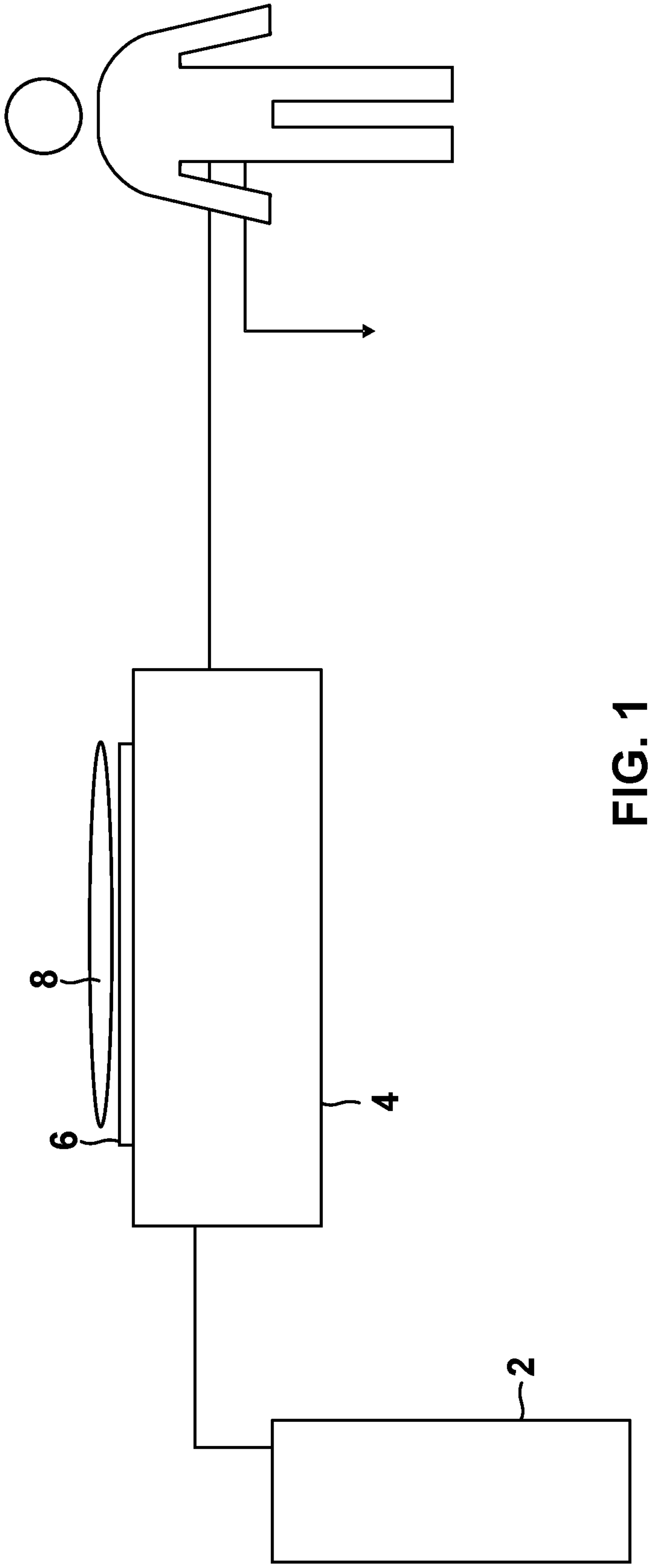
FIG. 1 is a schematic drawing illustrating an automated peritoneal dialysis machine.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "bag" as used herein refers to a container, and preferably a flexible, collapsible and/or foldable container. Preferably a bag is a container for fluids, most preferably for liquids.

The term "comprising" includes, but is not limited to, whatever follows the word "comprising." Use of the term indicates the listed elements are required or mandatory but that other elements are optional and may be present.

The term "concentrated" as used herein means, of a substance or solution, present in a high proportion relative to other substances, preferably having had fluid, such as water or other diluting agents, removed or reduced.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term “dialysate” describes a fluid into or out of which solutes from a fluid to be dialyzed diffuse through a membrane. An initial dialysate used for therapy typically contains electrolytes close in concentration to the physiological concentration of electrolytes found in blood. However, the concentration of the dialysate can change over the course of therapy, and can further be adjusted as desired.

The term “dialysis flow path” refers to a fluid pathway or passageway configured to convey a fluid, such as dialysate and/or blood, wherein said pathway forms at least part of, preferably the whole of, a fluid circuit for peritoneal dialysis, hemodialysis, hemofiltration, hemodiafiltration or ultrafiltration. A dialysis machine may be included within the flow path. A dialyzer may be included in the flow path.

The term “dissolution” as used herein refers to the process of a solute becoming incorporated into a solvent to make a solution. Dissolution means the same as “dissolving” and the terms are used interchangeably herein.

The term “dissolution time” as used herein refers to the time taken for one or more solutes to fully dissolve in a solvent to make solution. Dissolution times of the same solutes can be compared if the conditions of dissolution (including for example solvent type and volume, temperature, flow speed of solvent and container shape) are the same.

The term “fluid” can be any substance without a fixed shape that yields easily to external pressure such as a gas or a liquid. Specifically, the fluid can be water, preferably purified water, and can be water containing any solutes at any concentration. The fluid can be used as a solvent (to dissolve one or more solutes). The fluid can also be dialysate of any type including fresh, partially used, or spent. The fluid can also contain one or more dissolved gas. The fluid may be blood.

The term “fluidly connectable” refers to the ability to provide passage of fluid from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type. Most preferably the connections are provided by tubes or pipes.

The term “fluidly connected” refers to a particular state or configuration of one or more components such that fluid can flow from one point to another point. The connection state can also include an optional unconnected state or configuration, such that the two points are disconnected from each other to discontinue flow. It will be further understood that the two “fluidly connectable” points, as defined above, can from a “fluidly connected” state. The two points can be within or between any one or more of compartments, modules, systems, components, and rechargers, all of any type.

The term “formed” or “formed of” as used herein refers to a material comprising any of the materials, elements, composited or compounds listed.

The term “inlet” can refer to a portion of a component through which fluid and/or gas can be drawn into a component, conduit, or fluid passageway of any type, such as a bag, container, conduit, tube or pipe of any type.

The term “measuring” or “to measure” can refer to determining any parameter or variable. The parameter or variable can relate to any state or value of a system, component, fluid, gas, or mixtures of one or more gases or fluids.

The term “measurement” refers to data or information of the parameter or variable determined.

The term “mix” means to combine one or more substance so that the resulting mixture is not easily separated. Mixing, especially evenly spreading, of solute and solvent aids and speeds the process of dissolution. Mixing can be achieved by any method, including spraying, stirring, shaking or otherwise agitating. The term “improved mixing” refers to a situation wherein the components of a mixture are more evenly distributed and not clumped together. Improved mixing may be achieved, for example, by speeding the mixing up. In the context of a solution, improved mixing results in a solution of the correct concentration because all or most of the solutes dissolve, rather than remaining as clumps or aggregated within the solvent.

The term “nozzle” as used herein refers to a fitting, usually at the end of a tube or pipe, which controls the flow of a fluid (liquid or gas) through said fitting. It may control (in speed, direction or otherwise) the entry of the fluid into a container, especially a bag. It may accelerate or decelerate the fluid. It may control the direction of the fluid. The nozzle may control the density of spray of the fluid and direction of spray of fluid from the nozzle.

The term “outlet” refers to a portion of a component through which fluid or gas can be pulled out of said component and into another component, conduit, or fluid passageway of any type.

The term “pass through” refers to an action of fluid or gas passing a component positioned in a flow path. The fluid or gas can enter an inlet of the component and exit via an outlet of the component to continue the flow path.

The term “pressure” refers to a force exerted by a gas or liquid on the walls of a component, container, or conduit.

“Purified water” can be defined as water produced by distillation, deionization, reverse osmosis, or other suitable processes that remove impurities in water.

The term “reconstituting” or “re-constituting as used herein refers to restore to an original state. In the context of the solutions of the invention, this term is used to mean returning a solution to its original form, before liquids were removed, or in creating a solution from concentrated liquid and/or dried components.

The term “reconstituted” or “re-constituted” refers to an item, product or solution produced after reconstituting as defined above.

The term “solute” as used herein refers to a substance dissolved in a solution. The solute may comprise one or more chemicals or compounds. Solutes as used herein, before being dissolved in a solvent, may exist as entirely or partially dried, gels, concentrated liquids, pellets or powders, or any combination of these forms.

The term “solution” as used herein refers to a liquid mixture in which a solute is uniformly distributed within a solvent. A “solution for dialysis” may refer to any solution which can be used in any form of dialysis. It is envisaged that the solutions described herein contain specific concentrations of solutes.

The term “solvent” as used herein refers to a substance which dissolves a solute. Preferably the solvent is a liquid, and most preferably it is water.

As used herein, the “Venturi effect” reduction in fluid pressure, and increase in velocity, caused by a fluid flowing through a constricted section of a tube or pipe. Preferably the constriction is caused by a reduction in diameter of the tube or pipe.

The term "water purification unit" refers to any single component or system which can produce purified water (as defined above) from tap water or other water containing any type of impurity.

System

The present invention relates to an improved automated peritoneal dialysis machine that includes a preparator and cycler for in situ preparation of peritoneal dialysis fluid (PDF) for delivery and drainage from a patient.

The basic concept of an automated peritoneal dialysis machine is shown in FIG. 1 of the accompanying drawings. The machine is fluidly connected to a patient via a catheter and transfer set and the machine has a container or bag 2 with a fresh solution supply of peritoneal dialysis fluid (PDF) which is delivered to a heating bag 8 placed on a heat source, such as a heating plate 6 to warm the PDF prior to delivery to the patient. The fluid remains in the patient for a predetermined dwell time and then removed from the patient, normally being collected in a drainage bag. The parts are fluidly connectable to provide fluid paths through the system creating a fluid system which is controlled by a controller 4. The machine includes a pump for transport of the fluid to and away from the patient, valves to control the fluid flows, a heat source to warm the PDF prior to its introduction into the patient and sensors connected to a controller to monitor and control the process.

The coupling of the fluid paths to the machine may be conveniently achieved by the provision of a disposable cassette which includes connections to each fluid path. The cassette provides sterile, disposable fluid pathways and generally includes a pump region, valve region, a sensor region and optionally a heating region. The cassette has connections for coupling with the dialysate container, the catheter unit and the drainage outflow.

The machine controls and monitors the introduction of fresh PDF into the abdominal cavity via the inlet and transfer set and the elimination of waste fluid via the transfer set and outlet. Sequential treatment cycles are carried out on a patient, normally overnight. However, the production of sufficient PDF for these cycles, particularly in a home-based setting, can be problematic.

Figure 2:
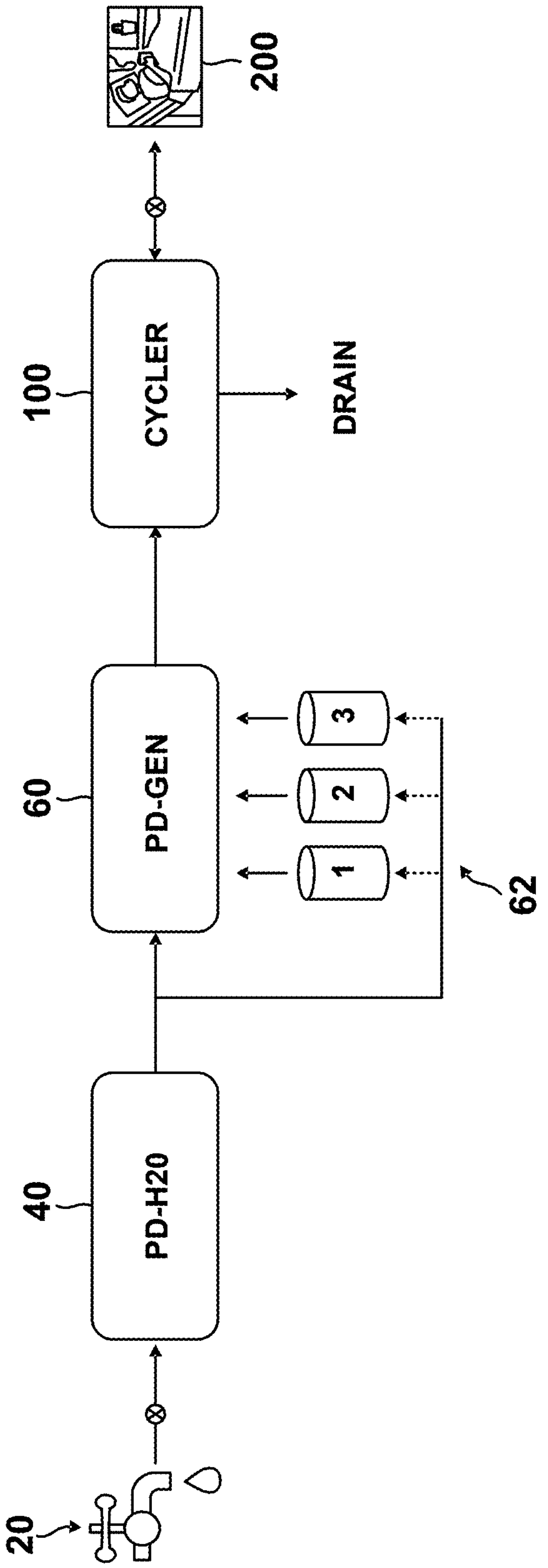
FIG. 2 is a block diagram of an automated peritoneal dialysis preparator and cycler machine for use with the present invention.

The Applicant has devised an improved modified peritoneal dialysis machine that includes a preparator as well as a cycler to form the peritoneal dialysis system. FIG. 2 of the accompanying drawings provides a high level block diagram of the preparator, including a purification system ("PD-H2O") 40 and a generation system ("PD-GEN") 60, and cycler ("CYCLER") 100. The system delivers water, such as purified drinking water from a tap 20, into one or more containers 62 ("1, 2, 3") with different powders to create a concentrate and then moves this concentrate to a mixing bag to create the peritoneal dialysis fluid. Drinking water is supplied to the purification system 40 and this purified water is then moved through powdered chemical constituents to create dissolution of the chemicals and proportioned in the generation system 60 to obtain the PDF for passing to the cycler 100. The powder concentrates may be provided in compartmentalized constituents bag with each compartment having an inlet and outlet with a two-way valve whereby purified water can enter each compartment and is then delivered to a mixing bag prior to delivery to the cycler 100. The cycler then delivers fresh PDF to the patient 200 and removes waste fluid via the drain outlet. This solves major problems on automated peritoneal diffusion, creating PDF starting from drinking water and containers with powders/concentrates, providing key benefits such as a reduction of the weight of the bags/containers that the patient has to handle; significant reduction of number, volume and weight of supplies; easier operation for patient; reduced infection risk; therapy customization and GDP reduction.

The combined peritoneal dialysis machine having a preparator as well as a cycler must be able to reconstitute powders (dissolve them in a liquid) and proportion them to create a pharma fluid suitable for delivery to a patient. Ideally, bags are provided that are equipped with nozzles to generate a turbulent flow, particularly using the Venturi effect, necessary to dissolve the powder and a hydraulic machine generates the flow to move different amounts of fluid. The system has a reconstitution part wherein the powders are dissolved and a proportioning part to proportion the right amount of concentrate formed from the dissolved powders.

The reconstitution part of the system includes the bags filled with the powders required to form the correct concentrate, such as dextrose, magnesium and calcium and lactate bicarbonate and sodium chloride. Electro valves are provided on entry and exit to the bags to deviate the flow path. A high pressure flow is required to ensure that the powders are completely dissolved, and a heater may be provided to aid dissolution and to raise the temperature of the resultant PDF. The proportioning part of the system requires a more accurate flow rate adjuster, such as a peristaltic pump, to move precise amounts of liquid in order to proportion the correct amount of concentrate, together with a scale system to measure the mass of the three solutions in order to proportion the right amount of concentrate.

However, one challenge with this system is to ensure that the correct proportion of water and concentrates are mixed to obtain the desired PDF, ideally being provided in a completely automated way. This is achieved by a volumetric approach that controls the hydraulic flow paths that introduce purified water to the powder concentrates, provide mixing of the concentrate to form the PDF and delivery of the freshly made PDF to the patient. In particular, different configurations of hydraulic flow/pressure generators are provided in the fluid paths to provide optimization of the flow of water through the fluid system to create the correct powder concentrates and subsequent peritoneal dialysis fluid for cycling. In preferred embodiments of the invention, some or all of the particular configurations are provided within one or more disposable cassette(s) having the appropriate inlet and outlet connections, a flow generator and a plurality of valves provided in the various fluid paths. For example, a cassette for the preparator may include an inlet connection, an outlet connection, at least one connector to the pure water source and a connector to each of the concentrate containers. A cassette for the cycler may include multiple connections to each solute container, a PDF bag connection, a patient line connector and a drain connector.

Figure 3:
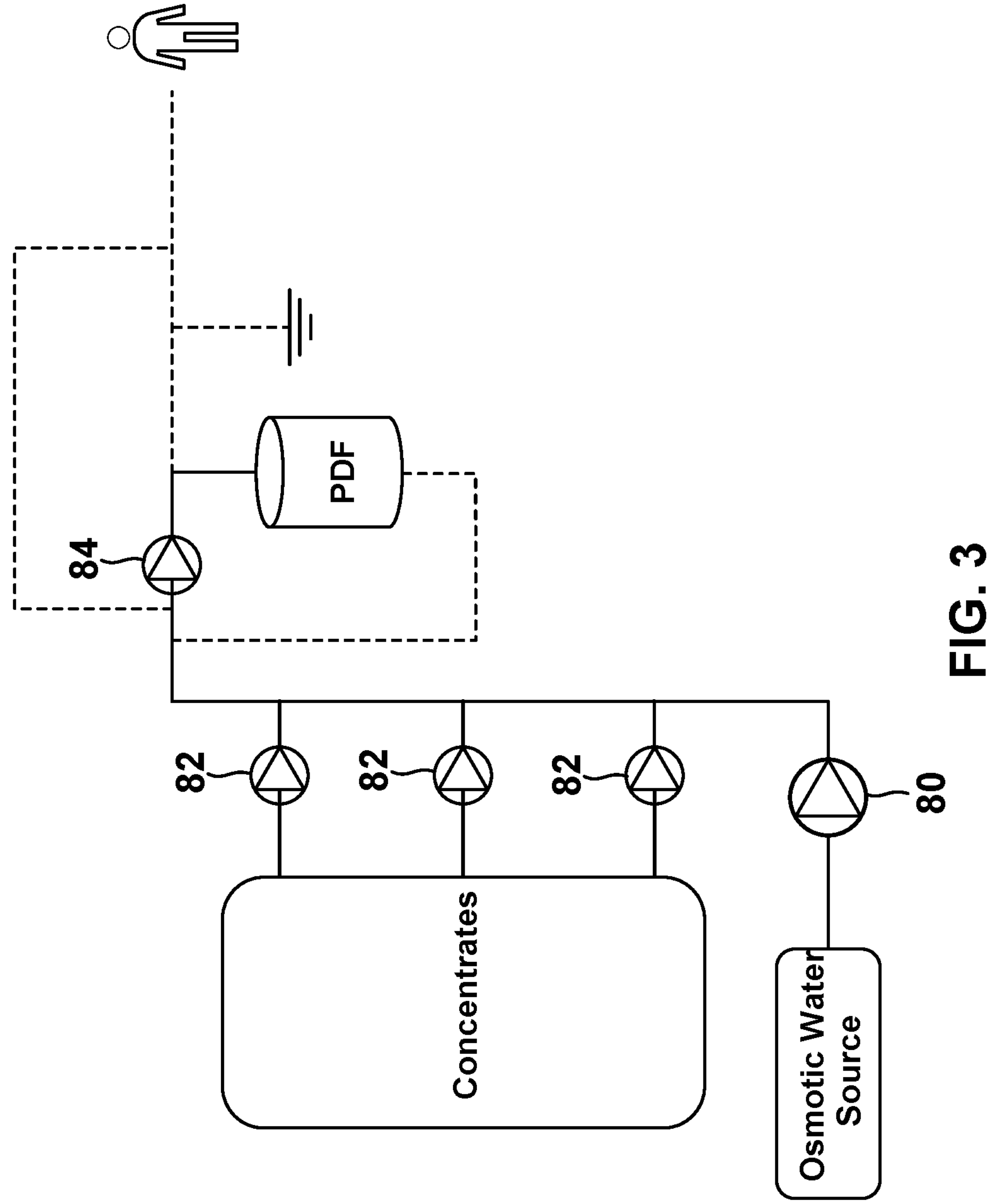
FIG. 3 is a schematic diagram of a disposable cassette according to one embodiment of the present invention for use in an automated peritoneal dialysis preparator and cycler machine.

The cassettes according to the present invention enable accurate control of hydraulic flow paths through the preparator and cycler. FIG. 3 of the accompanying drawings illustrates one embodiment of a hydraulic flow path according to the present invention. The hydraulic flow path is controlled by pressure generators provided in particular fluid paths of the fluid system. The pressure generators are preferably provided within a cassette (not shown) for coupling of the pathways to the purified water source, concentrate powder containers, inlet and outlet but alternatively, may be provided within disposable tubing provided for the different fluid paths of the system. In FIG. 3, five pressure generators are provided, four within the preparator and one within the cycler. A first pressure generator 80 controls purified water flow through the system, three pressure generators 82 control the introduction and mixing of powdered concentrates into the water flow and a fifth pressure generator 84 provides for accurate control of flow through the cycler. The fluid path is optimized in order to minimize production time using the three concentrate pressure generators 82 in parallel.

In the embodiment shown in FIG. 3 no mixing bag is required to mix the concentrate into the required solution due to highly optimized and accurate control and mixing of the powder with the purified water. Thus, this system may be regulated by a controller to provide online proportioning of the constituents making up the PDF.

Figure 4:
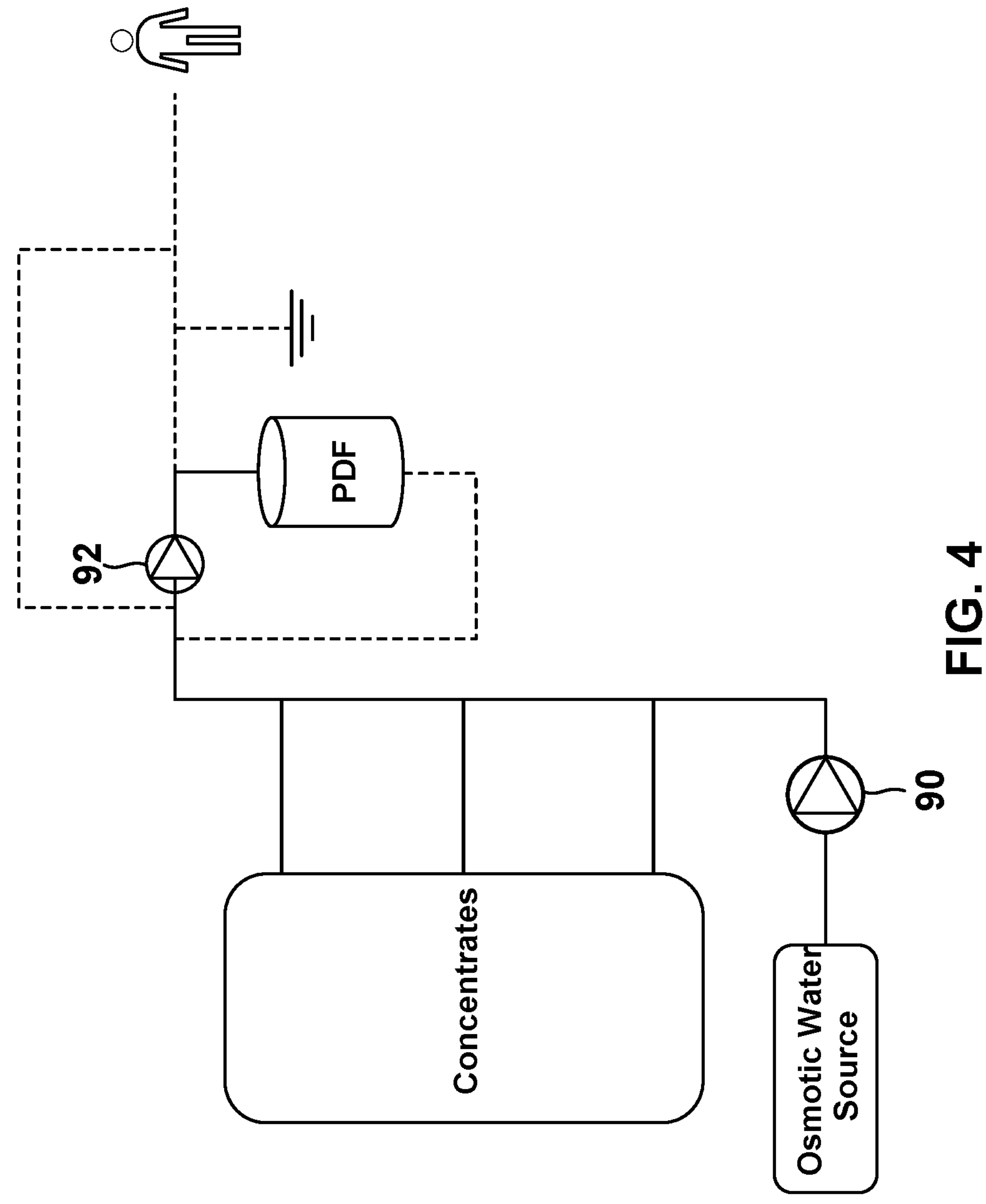
FIG. 4 is a schematic diagram of a disposable cassette according to another embodiment of the present invention for use in an automated peritoneal dialysis preparator and cycler machine.

An alternative embodiment of a hydraulic fluid path according to the invention is shown in FIG. 4. In this embodiment, two hydraulic flow/pressure generators 90, 92 are provided to create the hydraulic flow path through the preparator and cycler. The preparator is provided with a first pressure generator 90 for controlling purified water flow through the system and the cycler is provided with a second pressure generator 92 for regulating both the flow of concentrate mixed with the purified water and the cycler. The fluid path is optimized in order to minimize the number of components, with different types of pressure generators/actuators being provided having different characteristics. In this respect, the first for the control of purified water flow enables a high flow rate (ideally up to 400 ml/min) while the second provides a high accuracy stroke (ideally >2%, or 10 ml). Again, it is preferable for these components to be incorporated into at least one disposable cassette for installation in the machine.

Figure 5:
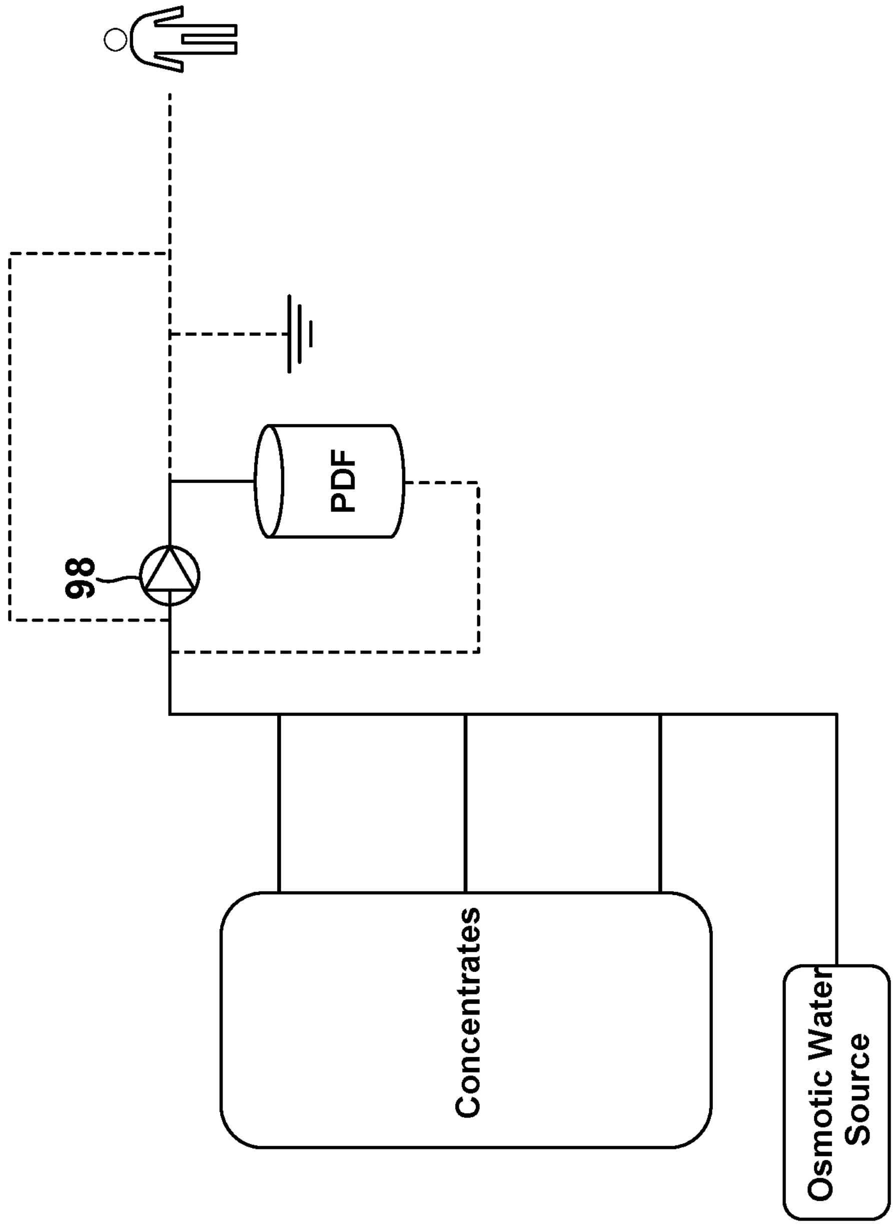
FIG. 5 is a schematic diagram of a disposable cassette according to yet another embodiment of the present invention for use in an automated peritoneal dialysis preparator and cycler machine.
Figure 6:
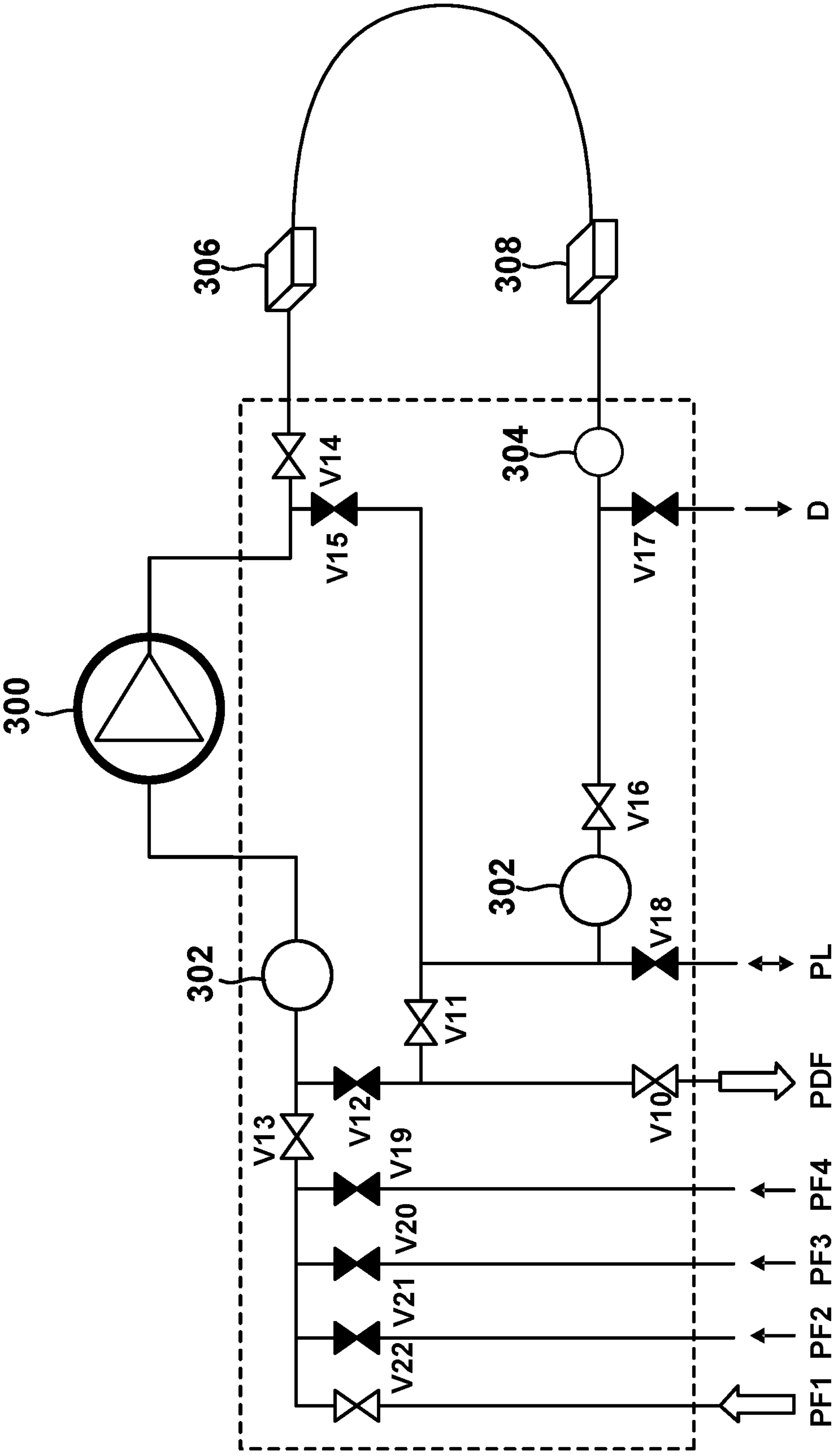
FIGS. 6 to 13 are schematic diagrams illustrating different fluid phases for a cassette fluid path of a cycler using pre-filled bags from a preparator of the system.
Figure 7:
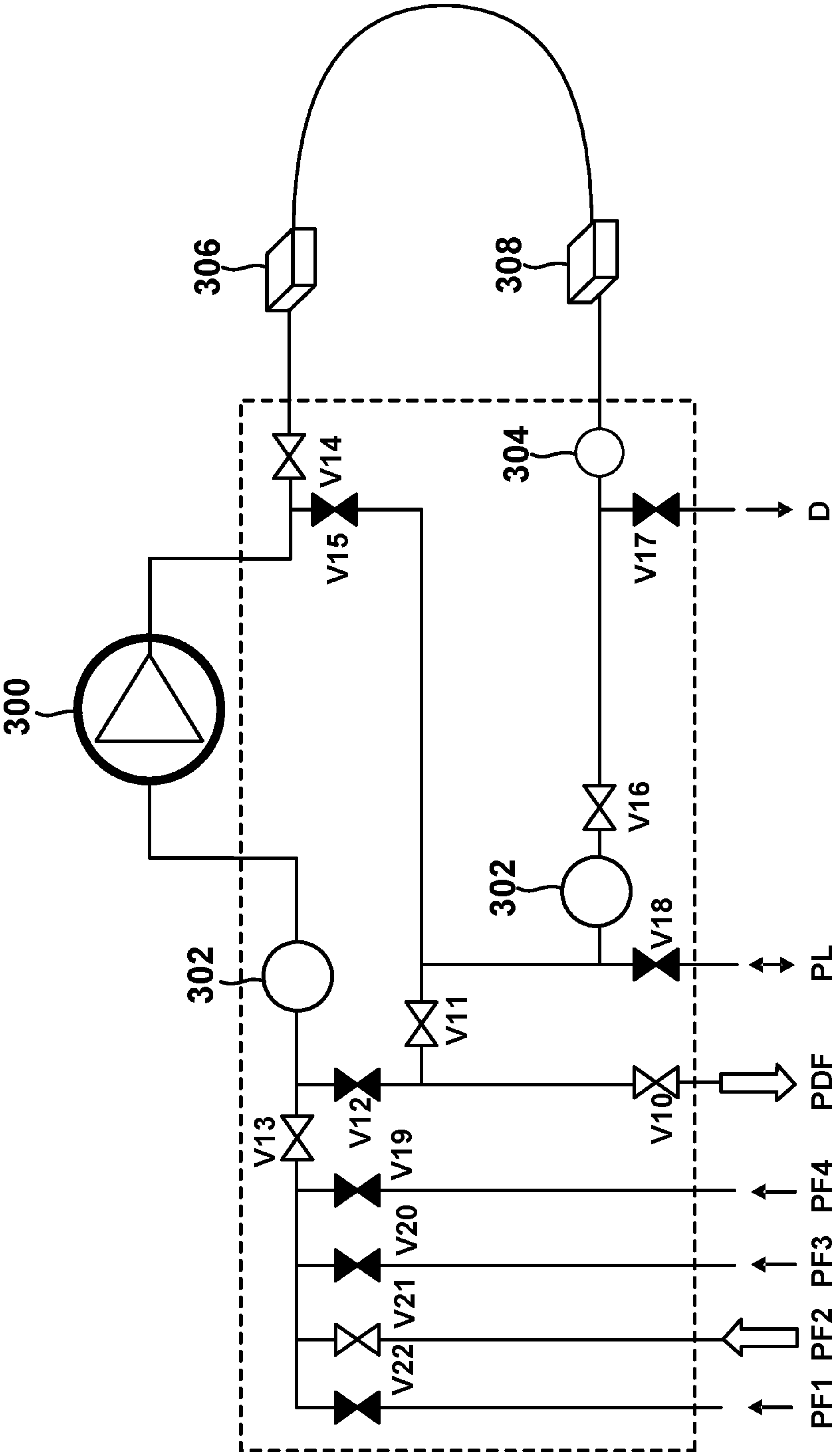
Figure 8:
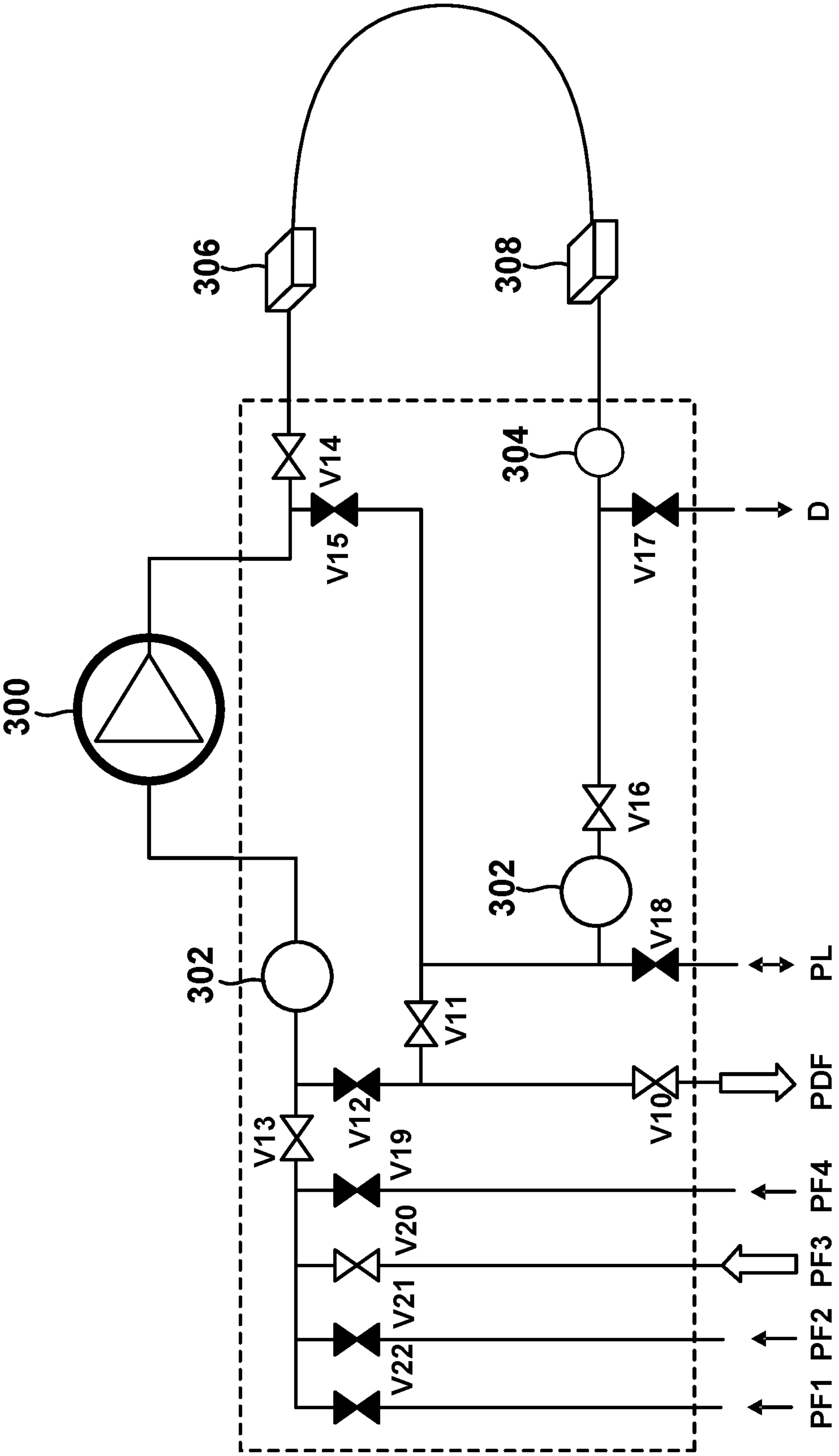
Figure 9:
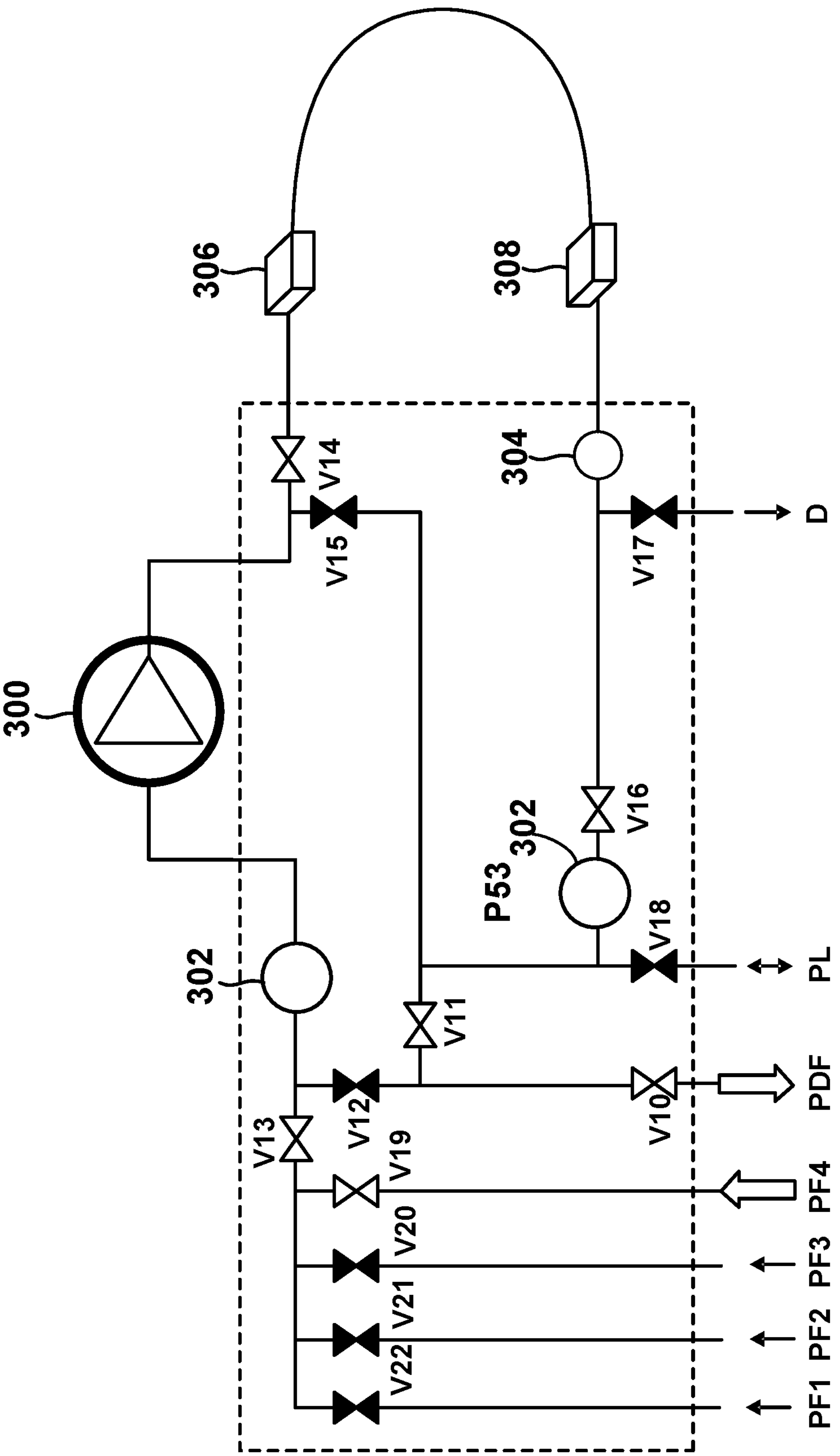

A further embodiment in shown in FIG. 5 of the accompanying drawings. In this embodiment, a single hydraulic variable flow/pressure generator 98 is provided in the cycler path to optimize the fluid path so that the correct PDF flows into the patient. This minimizes the number of components required in the system.

FIGS. 6 to 13 of the accompanying drawings illustrate fluid paths through a cycler cassette according to one embodiment of the present invention. The majority of the fluid paths and components would be incorporated into a disposable cassette albeit this is not shown in the drawings for the sake of simplicity. A single flow generator 300 in the form of a flexible pump is provided for movement of fluid through the lines with multiple valves V10 to V22 provided throughout the paths to open and close the various lines. The fluid path is also provided with a number of sensors, such as pressure sensors 302, temperature sensor 304, air sensor 306 and check sensor 308 to monitor and provide feedback on parameters within the cassette and the fluid path to and from the patient.

Figure 12:
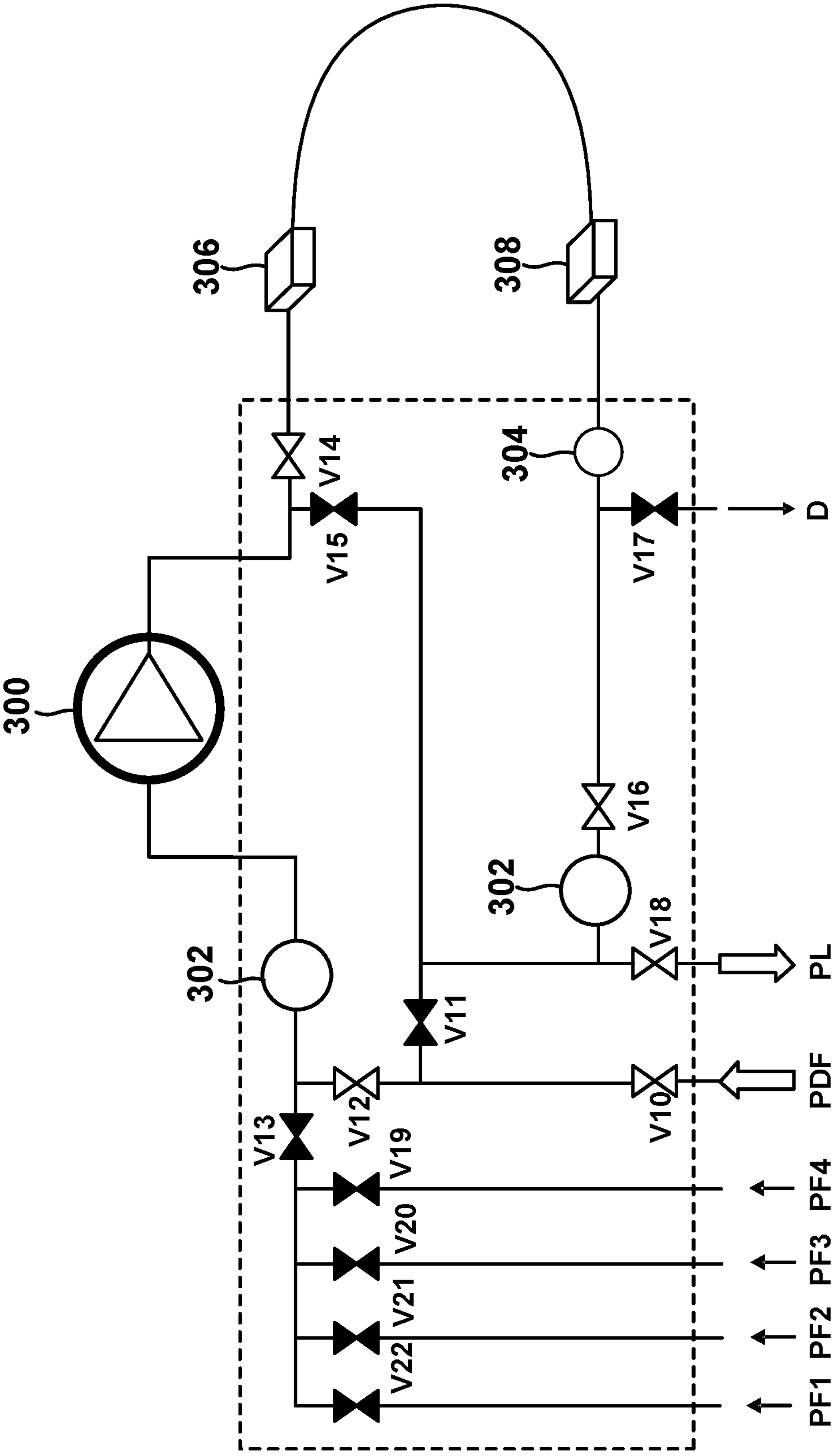
Figure 13:
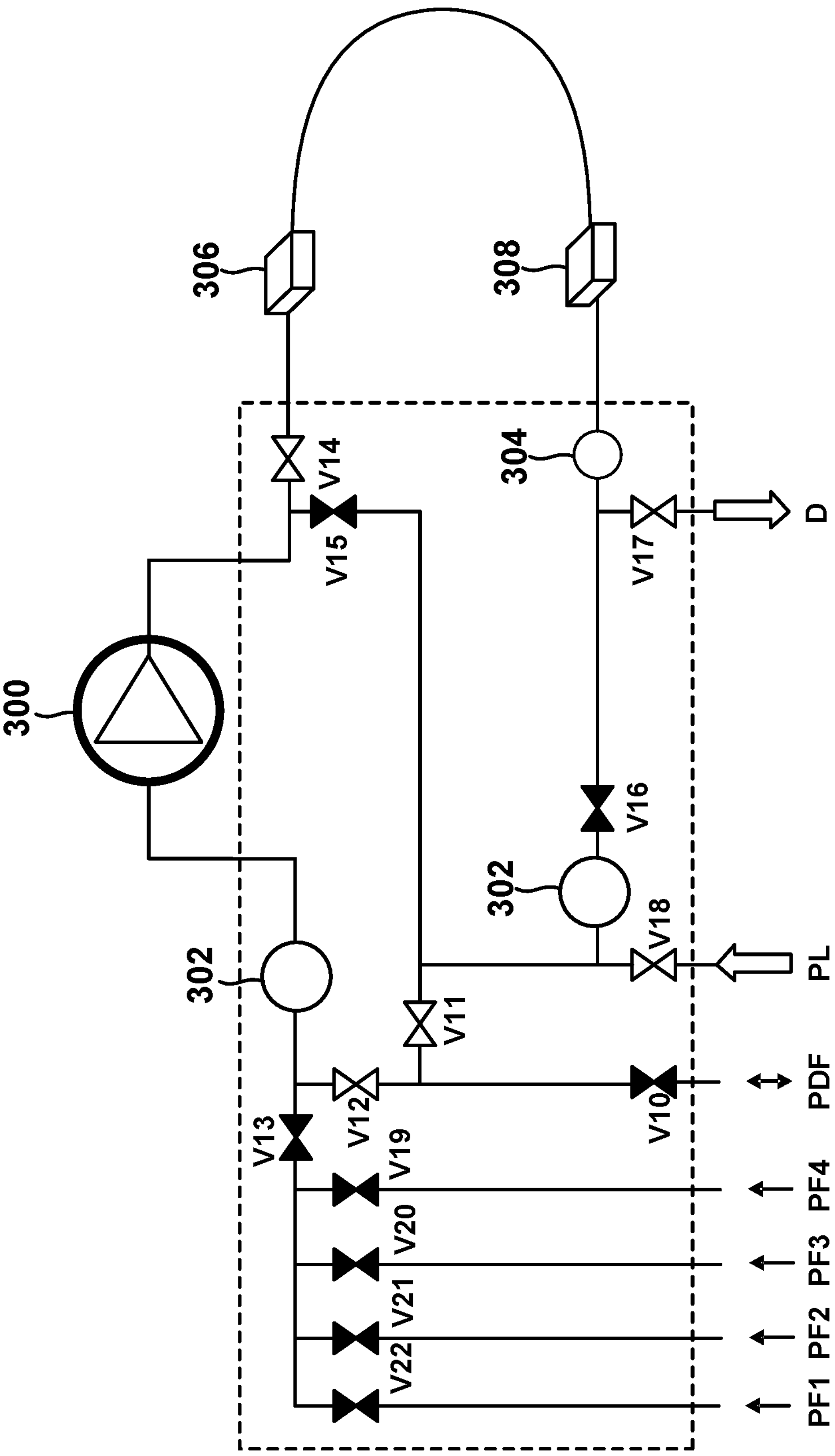

FIGS. 6 to 9 illustrate the filling of peritoneal fluid bag PDF by pre-filled solute bags PF1-PF4, followed by cassette priming (FIGS. 10 and 11), patient filling (FIG. 12) and draining of the patient line PL to drain line D (FIG. 13). Initial filling of the PDF bag by solute 1 (PF1) is achieved by opening valves V22, V13, V14, V16, V11 and V10 to create a fluid path between PF1 and PDF. All other valves are shut (indicated by black shading in the figures). PF2 is then added to the PDF bag by closing V22 and opening V21 (see FIG. 7). All other valve configurations remain the same. PF3 is then added by closing V21 and opening V20 (see FIG. 8), following by PF4 by closing V20 and opening V19 (see FIG. 9). The flow through the fluid path is controlled by the flexible pump 300 to provide correct mixing of the solutes in the PDF bag.

Figure 10:
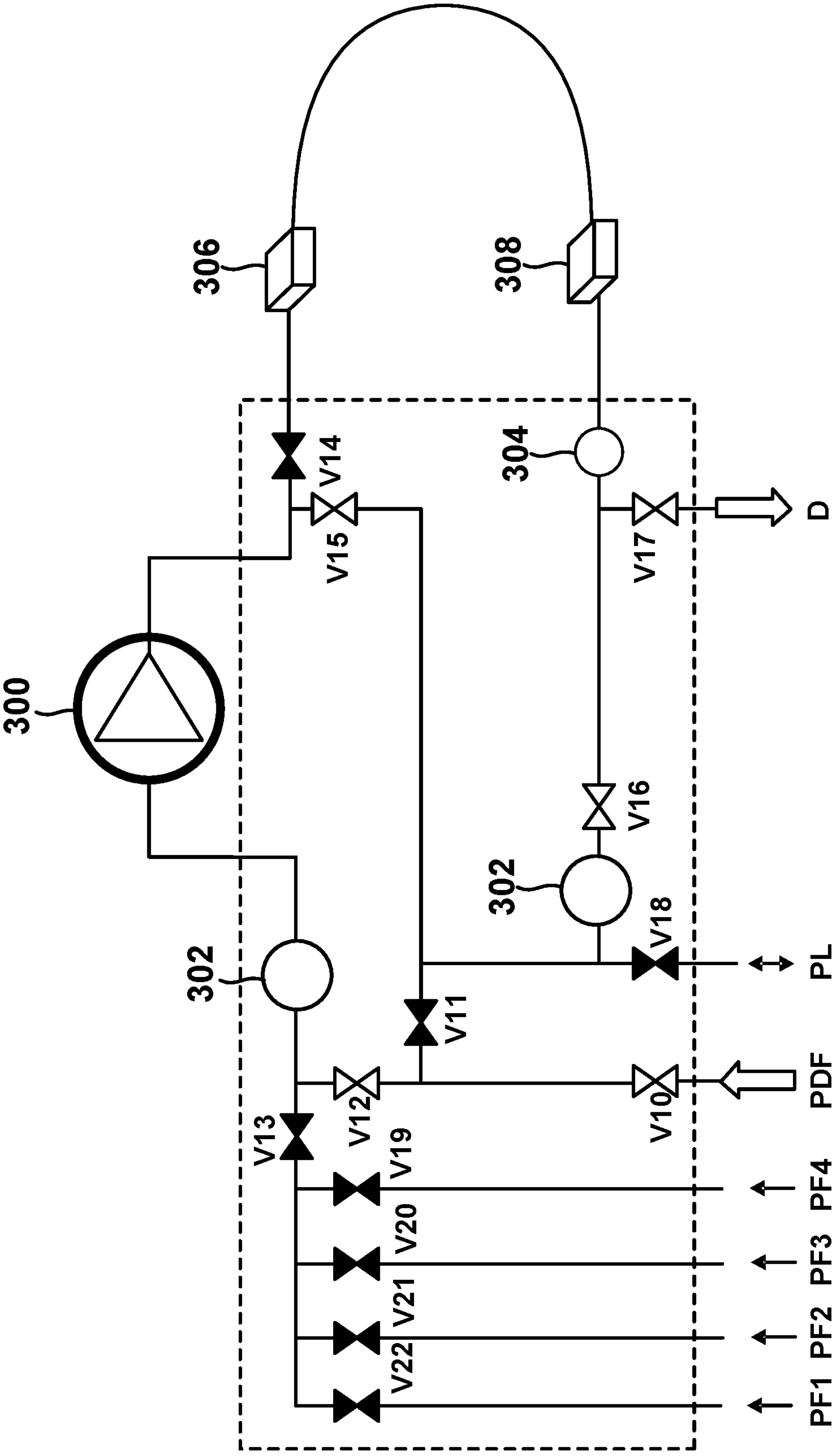
Figure 11:
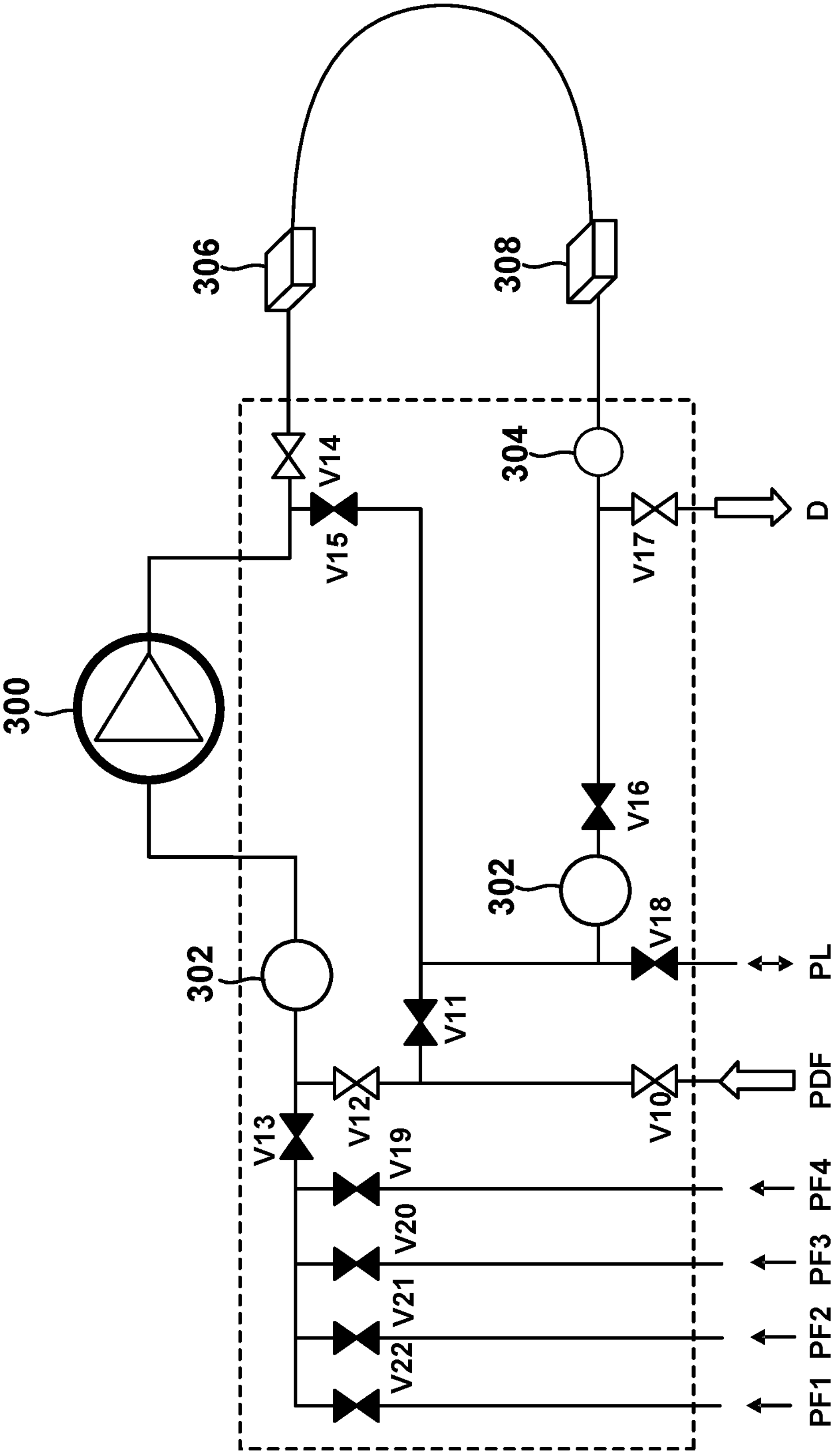

Once the peritoneal dialysis fluid has been created, the cassette enters a priming phase, as shown in FIGS. 10 and 11. In the first priming phase, V13 and V14 are also shut and valves V10, V12, V15, V16 and V17 are opened to enable the PDF to flow through and prime the patient line, followed by closing of V15 and V16 to allow priming to drain. Once fully primed, the cassette switches to patient filling phase, as shown in FIG. 12, by opening valves V16 and V18 and shutting V17. Draining of the patient line is then achieved by shutting valves V10 and V16 and opening valves V11 and V17 to drain. Thus, in the illustrated embodiment, a single flexible pump 300 provides for controlled fluid flow through the cassette.

This present invention provides an overall volume reduction in relation to the dialysis system due to the presence of reduced disposable component numbers. Furthermore, the system is more compact, providing cost savings with logistics and packaging.

It is to be appreciated that all parts of the system should be leak-proof so that fluids cannot escape. The container or bags of the system described herein may be made of any material, preferably a polymer, most preferably a plastic. The bag may be rigid or flexible. Preferably the bag is flexible, resistant and stretchable, most preferably in any direction. The bag may be made of a multi-layered material, or a single layered material.

The system preferably uses a bag containing a v-shaped, funnel shaped or cone shaped section, with the opening for the nozzle at the point of the cone. Such a shape maximises the mixing of the fluid spray leaving the nozzle with the solutes in the bag to aid dissolution. However, the bag can be replaced by a solid container, preferably shaped with a cone-shaped part in which to fit a nozzle. Said container may be a box or carton, and is preferably made of a plastic.

Examples of solutes may for example comprise the following or any combination thereof:—all electrolytes, powdered acids and bases, citric acid, sodium chloride, hydrogen carbonate, calcium and magnesium ions and salts, sodium, potassium, citric acid, sodium bicarbonate and all bicarbonate salt forms, sodium lactate, and osmotic agents such as glucose, dextrose, polydextrose, polydextrine and xylitol.

The dialysis system including optionally a cassette may include other conventional components of a dialysis machine, such as heating elements, controllers, sensors and scales. The system is particularly suitable for use in dialysis carried out at home, or another environment away from a hospital or medical practice. They may also be used in a hospital or any kind of medical practice.

One skilled in the art will understand that various combinations and/or modifications and variations can be made in the described apparatus, methods and uses depending upon the specific needs for operation. Moreover, features illustrated or described as being part of an aspect of the invention may be used in the aspect of the invention, either alone or in combination.

The invention claimed is:

1. A peritoneal dialysis system comprising:

a peritoneal dialysis preparator comprising a water source fluidly connectable to an inlet of each of a plurality of containers;

a cycler; and two or more hydraulic flow generators, each comprising at least one pump, wherein a first hydraulic flow generator of the two or more hydraulic flow generators is positioned in a fluid path between the water source and the plurality of containers as the only hydraulic flow generator in the fluid path between the water source and the plurality of containers, wherein the first hydraulic flow generator is configured to provide a high flow rate of water that is higher than a flow rate of a second hydraulic flow generator, wherein the second hydraulic flow generator of the two or more hydraulic flow generators is positioned in a fluid path between the plurality of containers and the cycler as the only hydraulic flow generator in the fluid path between the plurality of containers and the cycler, wherein the second hydraulic flow generator is configured to provide a high accuracy stroke that is higher than an accuracy of the first hydraulic flow generator, and wherein each container of the plurality of containers includes one or more solutes for dissolution of the one or more solutes to form a peritoneal dialysis fluid for delivery to the cycler for delivery to and drainage from a patient.

2. The system of claim 1, wherein each container of the plurality of containers is fluidly connectable to a chamber configured to receive a solution of each of the one or more solutes for preparation of the peritoneal dialysis fluid, the chamber being fluidly connectable to the cycler.

3. The system of claim 1, wherein the hydraulic flow generator is a variable flow generator providing an operative flow range of 50-400 milliliters per minute (ml/min).

4. The system of claim 1, wherein the first hydraulic flow generator is positioned in the fluid path between the water source and the plurality of containers to increase dissolution of the one or more solutes, mixing of solutions formed from the one or more solutes, or cycling of the peritoneal dialysis fluid thus formed.

5. The system of claim 1, wherein the second hydraulic flow generator is positioned in the fluid path between the plurality of containers and the cycler for controlled movement of the formed peritoneal dialysis fluid.

6. The system of claim 5, wherein the second hydraulic flow generator in the fluid path between the plurality of containers and the cycler is configured to provide the high accuracy stroke providing >2 percent (%) or 8-12 ml accuracy.

7. The system of claim 1, wherein the plurality of containers include three containers each fluidly connectable to the water source.

8. A disposable cassette for a dialysis machine, the cassette comprising:

at least one peritoneal dialysis fluid (PDF) connector to a peritoneal dialysis fluid source, at least one patient line connector to a patient line, at least one drain line connector to a drain line, a plurality of solute connectors to a plurality of solute containers, and only one hydraulic flow generator, wherein the cassette defines a plurality of fluid paths including:

a first fluid path between the plurality of solute connectors and the at least one PDF connector, a second fluid path between the at least one PDF connector and the at least one patient line connector, and a third fluid path between the at least one patient line connector and the at least one drain line connector, wherein the only one hydraulic flow generator is a pump positioned in:

the first fluid path between the plurality of solute connectors and the at least one PDF connector, the second fluid path between the at least one PDF connector and the at least one patient line connector, or the third fluid path between the at least one patient line connector and the at least one drain line connector, and wherein the cassette is configured to generate flow in a single direction through the pump.

9. The cassette of claim 8, wherein the cassette has a plurality of valves, and wherein each valve of the plurality of valves is positioned in a different first fluid path, a different second fluid path, or a different third fluid path of the plurality of fluid paths.

10. The cassette of claim 8, wherein the only one hydraulic flow generator is a positive displacement pump.

11. A disposable cassette for a dialysis machine, the cassette comprising:

a water source outlet configured to fluidly connect to an outlet of a water source, at least one solute inlet configured to fluidly connect to an inlet of a container of solute, a first fluid path between the water source outlet and each solute inlet of the at least one solute inlet, a peritoneal dialysis fluid (PDF) inlet configured to fluidly connect to an inlet of a PDF chamber, at least one solute outlet configured to fluidly connect to an outlet of the container of solute, a second fluid path between each solute outlet of the at least one solute outlet and the PDF inlet for flow of a solution formed from the solute in the container, and one or more hydraulic flow generators, wherein at least one hydraulic flow generator of the one or more hydraulic flow generators comprises a pump positioned in at least one of:

the first fluid path between the water source outlet and each solute inlet of the at least one solute inlet, or the second fluid path between each solute outlet of the at least one solute outlet and the PDF inlet, wherein the cassette is configured to generate flow in a single direction through the pump.

12. The cassette of claim 11, wherein the at least one hydraulic flow generator of the one or more hydraulic flow generators is included in the second fluid path between each solute outlet of the at least one solute outlet and the PDF inlet.

13. The cassette of claim 11, wherein the at least one hydraulic flow generator of the one or more hydraulic flow generators is included in the first fluid path between the water source outlet and each solute inlet of the at least one solute inlet.

14. The cassette of claim 11, further comprising a plurality of containers of solute including the container, wherein a hydraulic flow generator of the one or more hydraulic flow generators is provided in a fluid path between the water source outlet and each container of the plurality of containers of solute.

15. The cassette of claim 14, wherein the at least one solute inlet includes three solute inlets configured to connect to three separate solute containers of the plurality of containers of solute or three separate compartments of the container, and wherein each fluid path between the water source outlet and each solute inlet of the at least one solute inlet includes a hydraulic flow generator of the one or more hydraulic flow generators.

16. The cassette of claim 11, wherein the at least one hydraulic flow generator of the one or more hydraulic flow generators includes a first hydraulic flow generator provided in the first fluid path between the water source outlet and each solute inlet of the at least one solute inlet, wherein the first hydraulic flow generator is a high flow rate generator, wherein the at least one hydraulic flow generator of the one or more hydraulic flow generators includes a second hydraulic flow generator provided in the second fluid path between each solute outlet of the at least one solute outlet and the PDF inlet, and wherein the second hydraulic flow generator is a high accuracy flow generator having a higher accuracy and a lower flow rate than the first hydraulic flow generator.

17. The cassette of claim 11, wherein the at least one hydraulic flow generator is a kinetic pump.

* * * * *